United States Patent [19]

Buteau et al.

[11] Patent Number: 5,585,076
[45] Date of Patent: Dec. 17, 1996

[54] INSTALLATION FOR SUBJECTING SUBSTANCES PACKAGED IN FLEXIBLE PACKETS TO HIGH PRESSURE TREATMENT

[75] Inventors: Fabrice Buteau, Basse Goulaine; Bernard Ollivaud, Le Cellier, both of France

[73] Assignee: GEC Alsthom ACB, Paris, France

[21] Appl. No.: 499,773

[22] Filed: Jul. 6, 1995

[30] Foreign Application Priority Data

Jul. 12, 1994 [FR] France .................. 94 08627

[51] Int. Cl.⁶ .................. A23L 3/04; A23L 3/015
[52] U.S. Cl. .................. 422/295; 99/360; 99/371
[58] Field of Search .................. 422/295; 99/360, 99/371

[56] References Cited

U.S. PATENT DOCUMENTS

| | | | |
|---|---|---|---|
| 5,165,325 | 11/1992 | Akatsu | 422/39 |
| 5,213,029 | 5/1993 | Yutaka | 422/295 |
| 5,316,745 | 5/1994 | Ting et al. | 422/295 |
| 5,470,547 | 11/1995 | Lhenry | 422/295 |

FOREIGN PATENT DOCUMENTS

| | | |
|---|---|---|
| 0480422A2 | 4/1992 | European Pat. Off. . |
| 0588010A1 | 3/1994 | European Pat. Off. . |
| 2442018 | 6/1980 | France . |
| 2687590 | 8/1993 | France . |

*Primary Examiner*—Robert J. Warden
*Assistant Examiner*—Theresa T. Snider
*Attorney, Agent, or Firm*—Sughrue, Mion, Zinn, Macpeak & Seas

[57] ABSTRACT

The installation, which includes a tubular enclosure, is provided with a plugging device at each end, each plugging device including a moving assembly that can be displaced perpendicularly to the axis Δ of the enclosure. The moving assembly includes a plug of the stopper type provided with a seal, a spacer provided with a pull rod a drawer and a plugging body. The moving assembly is slidably mounted in a force take-up member. Via co-operation between sloping ramps carried by the plug and complementary sloping grooves in the drawer, the transverse displacement of the drawer causes the plug to be displaced axially.

6 Claims, 8 Drawing Sheets

INSTALLATION FOR SUBJECTING SUBSTANCES PACKAGED IN FLEXIBLE PACKETS TO HIGH PRESSURE TREATMENT

The present invention relates to an installation for subjecting substances packaged in flexible packets to high pressure treatment.

BACKGROUND OF THE INVENTION

Particularly but not exclusively, the invention may be applied to food substances. It is known that subjecting food substances to very high pressures, in the range 2,000 bars to 10,000 bars is developing extensively.

Such an installation constitutes an autoclave which essentially comprises a tubular enclosure closed at each of its ends by a respective plugging device.

OBJECTS AND SUMMARY OF THE INVENTION

An object of the invention is to provide such an installation that includes plugging devices enabling fast opening and closing to be effected.

To this end, the invention provides an installation for subjecting substances packaged in flexible packets to high pressure treatment, the installation including a tubular enclosure of axis Δ that is provided with a plugging device at each of its ends, wherein each of said plugging devices includes a moving assembly that can be displaced in a transverse direction γ that is perpendicular to the axis Δ, said moving assembly being supported by a force take-up member in which it can slide between two abutment end positions, said plugging device including a plug of the stopper type including a male portion which is provided with a seal, and which penetrates into the bore in the tubular enclosure, the plug being axially displaced by co-operating with a drawer via a set of ramps and sloping grooves, said drawer being mounted to slide in said transverse direction γ between two stop positions on a plugging body which is itself slidably mounted in said force take-up member, the end position in one direction of said drawer and of said plugging body guaranteeing that the enclosure is fully open with the plug being both axially and transversely disengaged from the bore in the tubular enclosure, an association of orifices further guaranteeing, in that end position, an unobstructed axial passage to the bore in the tubular enclosure.

According to another characteristic, said plug is provided with a stem which penetrates into an orifice in said plugging body.

According to another characteristic, when the plugging device is in the closed position, a spacer is disposed between said plug and said plugging body.

In a particular embodiment, the spacer is provided with a pull rod via which to apply traction in said transverse direction γ, such traction being applied to said rod causing the spacer to be disengaged by being displaced until it comes into abutment against one end of said drawer, whereupon, with the movement being continued, it drives the drawer with it until the drawer comes into abutment against a stop on the plugging body, whereupon the plugging body is displaced to the final open position in which it abuts against the force take-up member.

BRIEF DESCRIPTION OF THE DRAWINGS

An embodiment of the invention is described below with reference to the accompanying drawings, in which.

DETAILED DESCRIPTION OF THE PREFERRED EMBODIMENT

Figure 1:
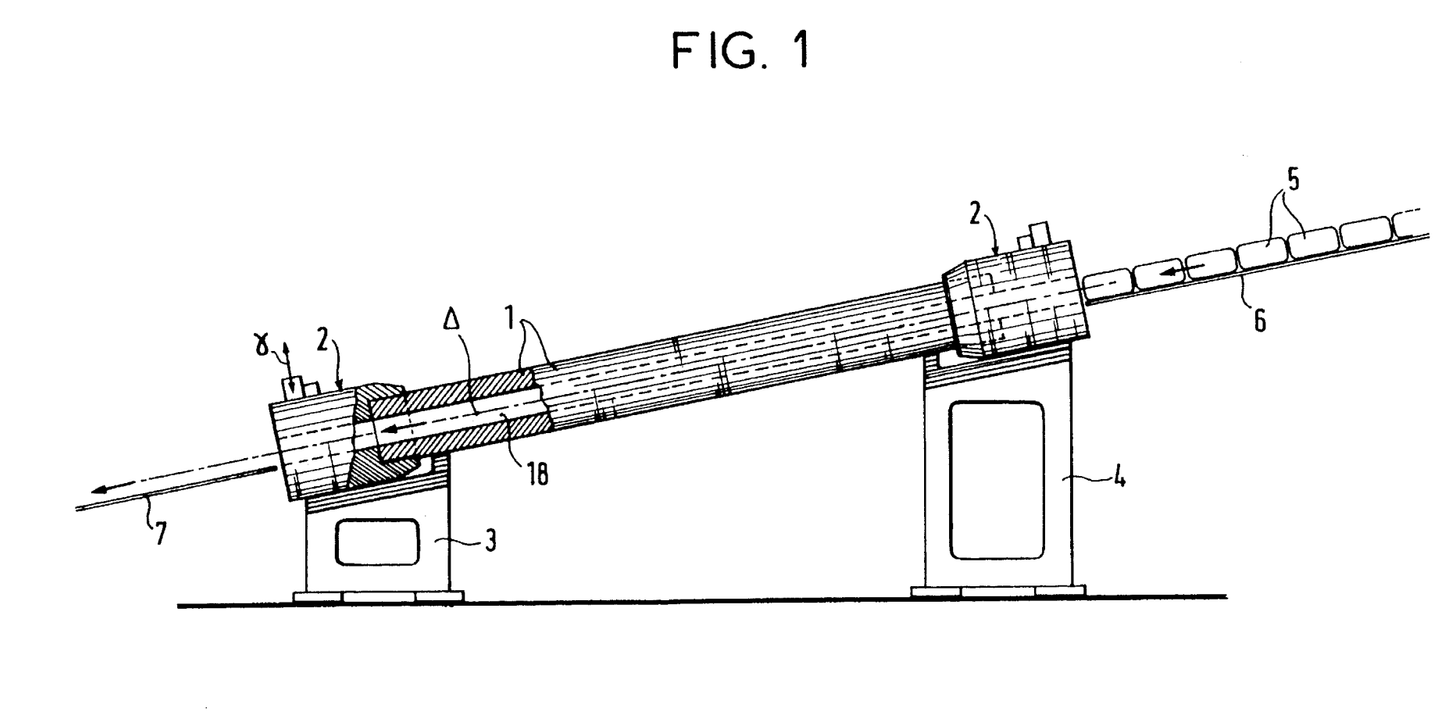
FIG. 1 is a diagram showing an installation of the invention for subjecting substances packaged in flexible packets to high pressure treatment.

FIG. 1 shows an installation for subjecting substances packaged in flexible packets to high pressure treatment.

The installation essentially comprises a tubular enclosure 1 of axis Δ that is provided with a plugging device 2 at each of its ends.

The installation rests in a sloping position on supports 3 and 4 enabling flexible packets 5 containing the substances that are to be subjected to high pressure treatment to be loaded and unloaded merely by gravity respectively on a loading ramp 6 and on an unloading ramp 7.

The enclosure is filled with water while the packets are being loaded.

Once the enclosure has been closed, the high pressure treatment is performed by the water that has been fed into the enclosure.

Figure 2:
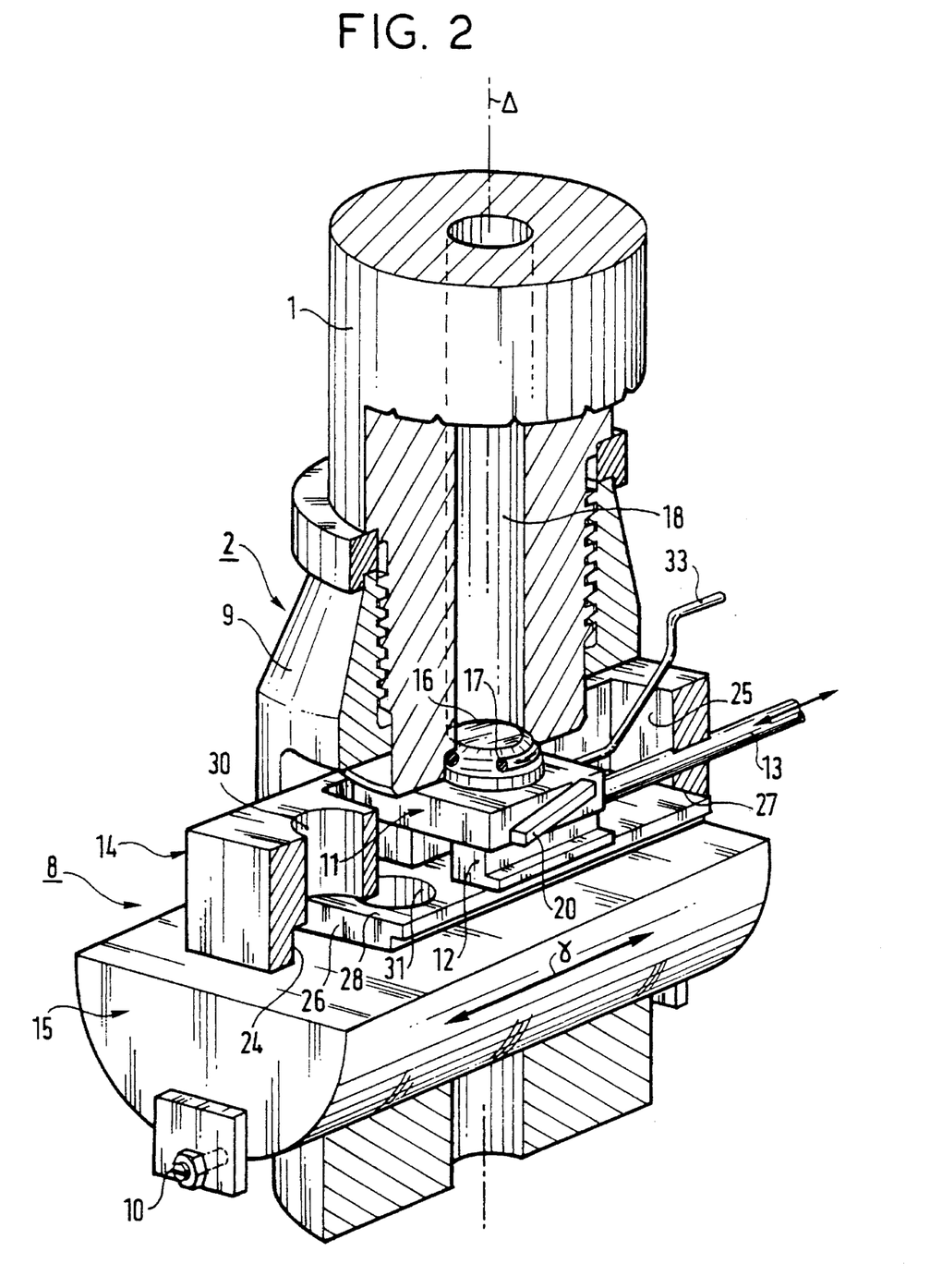
FIG. 2 is a partially cut-away perspective view of a plugging device, one of which is disposed at each end of the installation shown in FIG. 1, in which the plugging devices are referenced 2.
Figure 7:
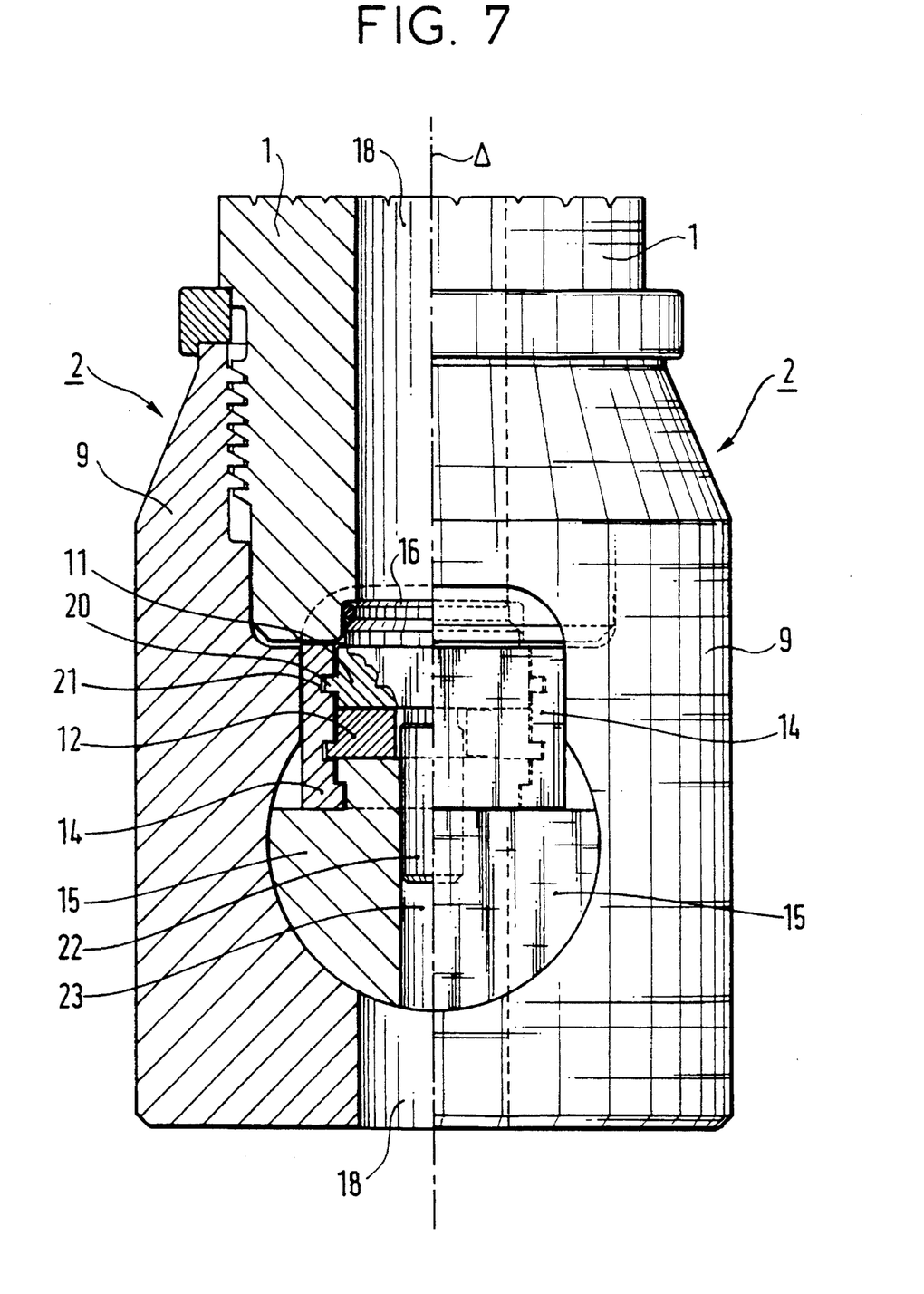
FIG. 7 is a half-section view on VII—VII of FIG. 3.

A plugging device such as 2 is described below with reference to FIGS. 2, 3, and 7.

The device includes a moving assembly 8 supported in a yoke 9 screwed onto the end of the tubular enclosure 1. The yoke 9 constitutes a force take-up member in which the moving assembly is mounted to slide between two end positions limited by abutments 10, the assembly 8 being displaced in a transverse direction γ that is perpendicular to axis Δ.

The moving assembly 8 comprises a plug 11, a spacer 12 provided with a pull rod 13, a drawer 14, and a plugging body 15.

The plug 11 is of the stopper type including a male portion 16 which is provided with an O-ring seal 17, and which penetrates into the bore 18 in the tubular enclosure 1. FIG. 3A, showing the detail referenced A in FIG. 3, shows that the plug 11 is also provided with an anti-extrusion ring 19. The plug 11 is provided with a set of side ramps 20 which co-operate with complementary sloping grooves 21 (FIG. 7)

provided in the drawer 14 that is slidably mounted on the plugging body 15.

The plug 11 is provided with a stem 22 which penetrates into an orifice 23 in the plugging body 15 for guiding the plug in axial displacement along axis Δ. The axial displacement of the plug 11 is caused by the drawer 14 sliding in the transverse direction γ by means of the movement being transformed by the ramps and grooves 20, 21 co-operating with one another. The sliding stroke of the drawer 14 on the plugging body 15 is limited between two end stop positions by the front and rear faces 24 and 25 of the drawer 14 abutting against the end faces 26 and 27 of a T-shaped section member 28 for guiding the drawer, which member is part of the plugging body 15.

Figure 6:
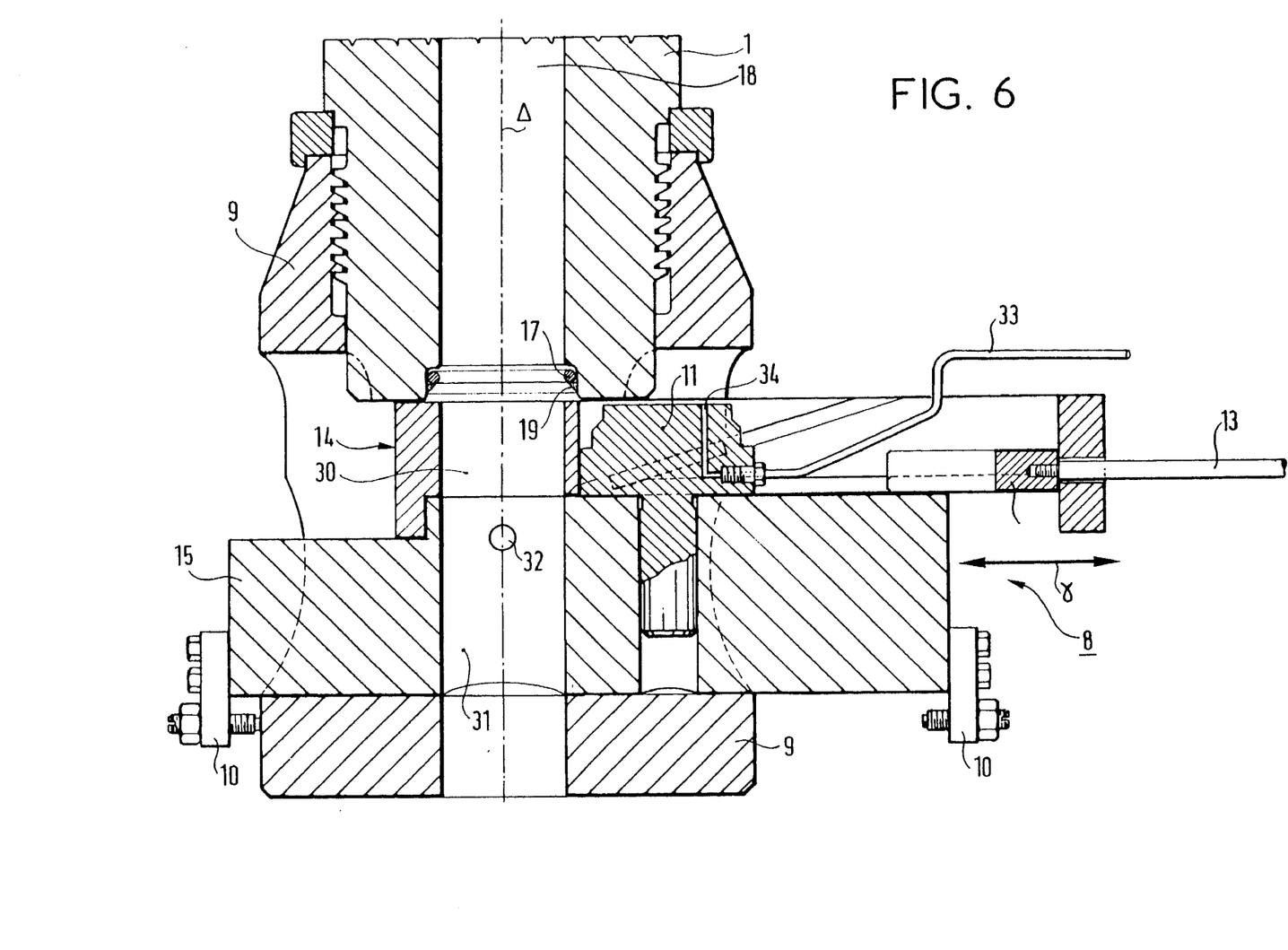
FIG. 6 is an axial section view of the plugging device in the fully-open position, the plug being disengaged transversely from axis Δ of the tubular enclosure, and an association of orifices providing an unobstructed axial passage to the bore in the tubular enclosure.

The spacer 12 is a spacer in the form of a fork having two prongs flanking the stem 22 of the plug, and it is situated between the plug and the plugging body 15. The spacer is mounted to slide in the drawer 14 between two end positions delimited by the rear face 25 of the drawer 14 and by an inside face 29 thereof. The drawer 14 is further provided with a hole 30, and the plugging body 15 is further provided with a hole 31, which holes coincide with the bore 18 in the enclosure 1 when the plugging device is in the open position as shown in FIG. 6.

Figure 3:
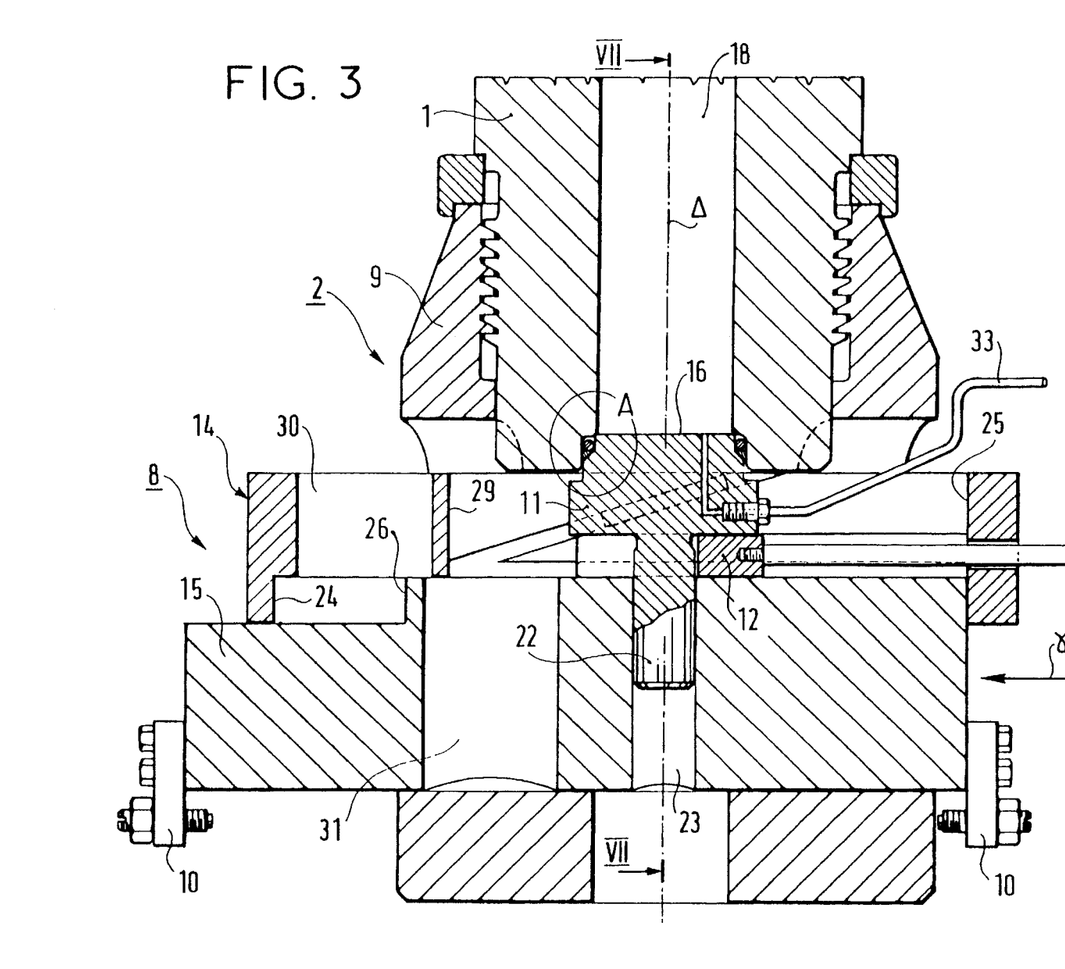
FIG. 3 is an axial section view of a plugging device as shown in FIG. 2, in the closed position.
Figure 3A:
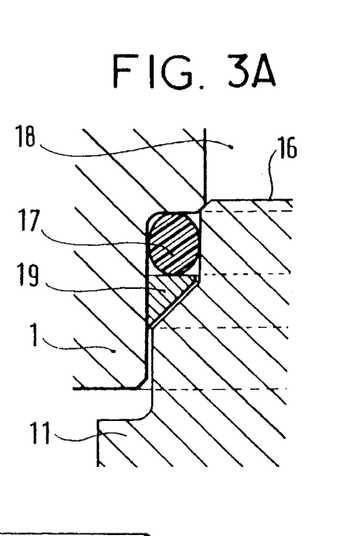
FIG. 3A shows detail A of FIG. 3.

FIG. 3 shows the plugging device in the closed position. The spacer 12 is situated under the plug 11 which penetrates into the bore 18 in the enclosure 1, the drawer 14 abuts leftwards against the right end face 27 of the T-shaped section member 28 of the plugging body 15, and the plugging body also abuts leftwards via abutment 10 against the yoke 9.

Figure 4:
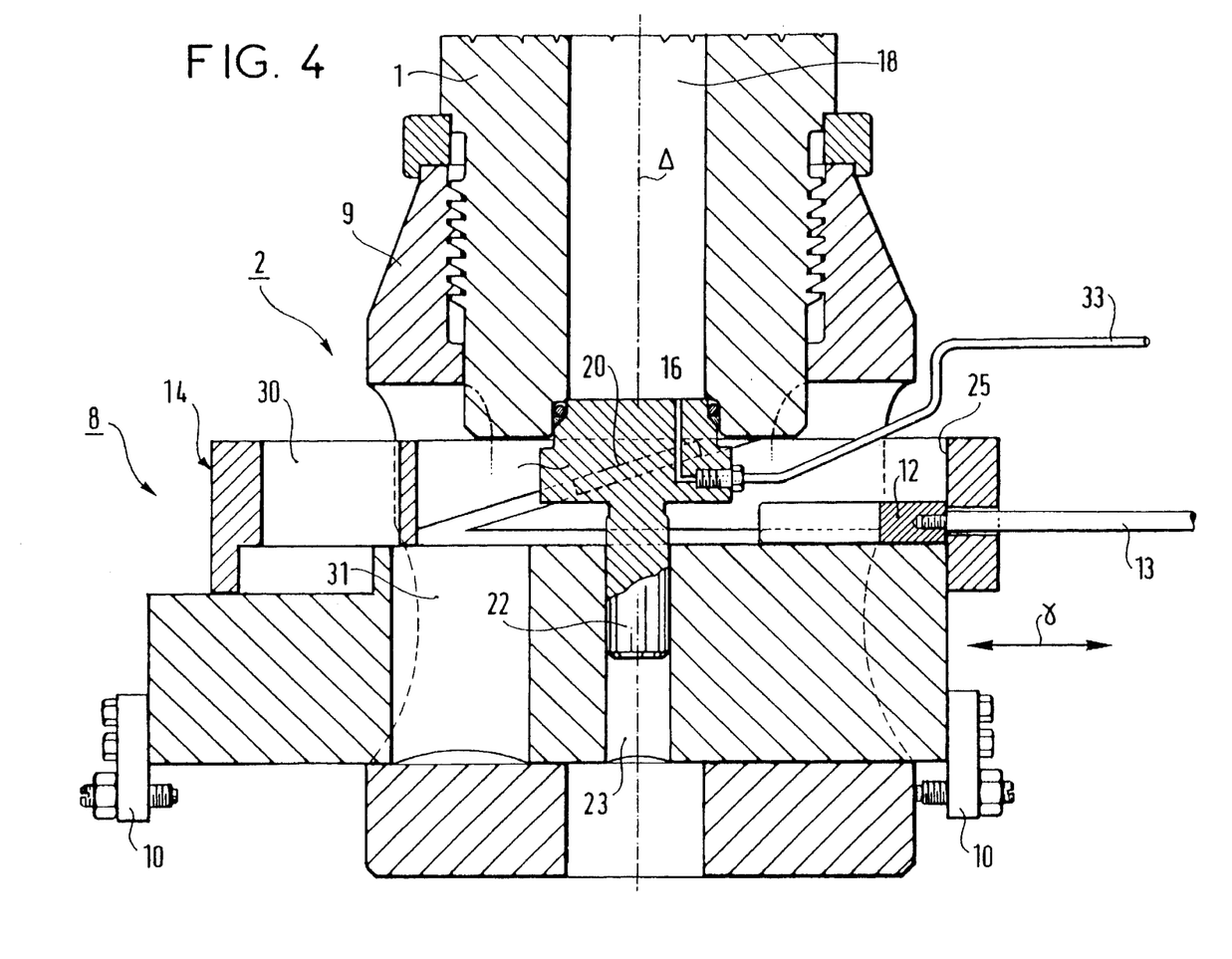
FIG. 4 is an axial section view of a plugging device in a position in which the spacer of the plug is disengaged and comes into abutment against one end of the drawer.
Figure 5:
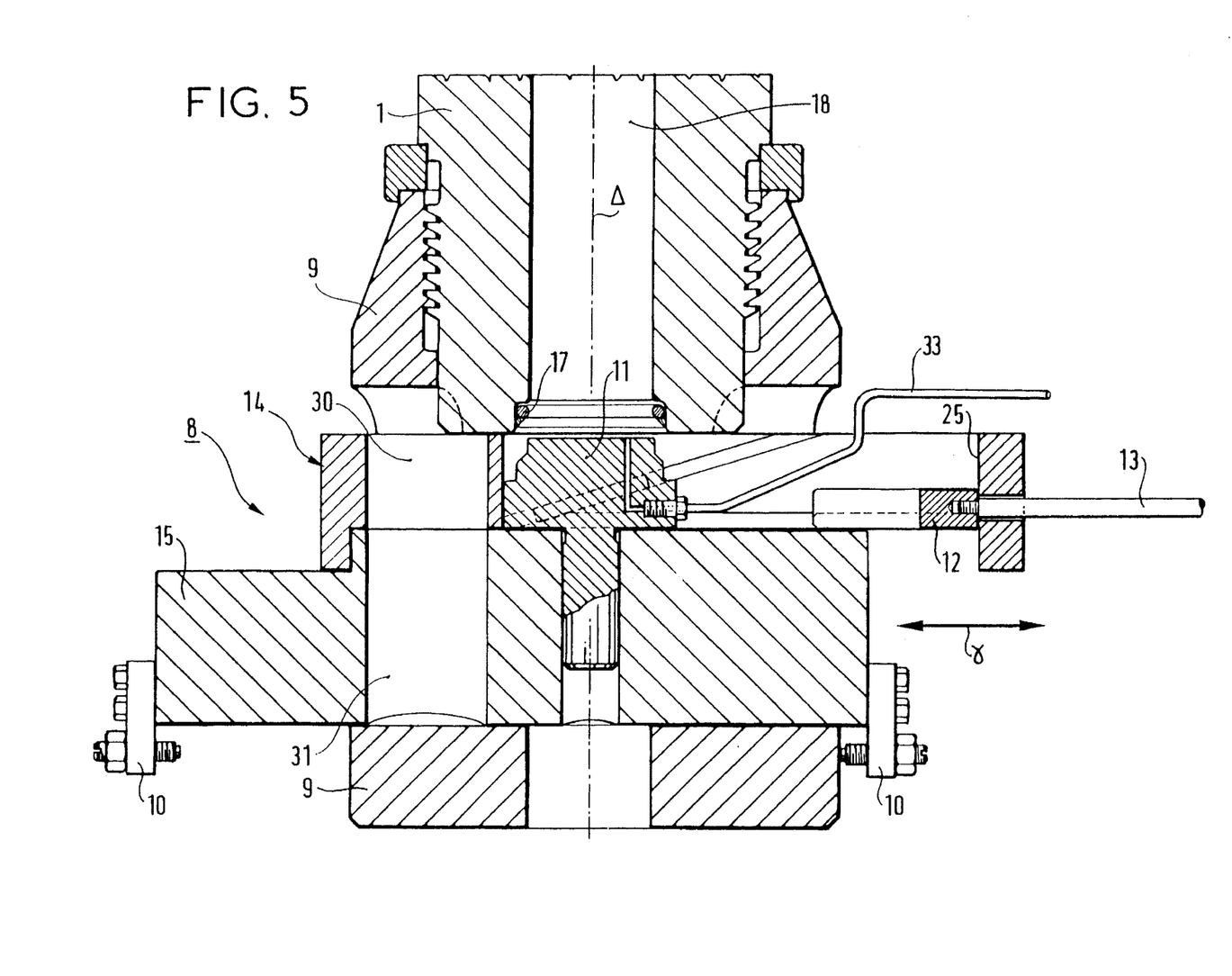
FIG. 5 is an axial section view of the plugging device in a position in which the drawer comes into abutment against a stop on the plugging body, the plug being axially disengaged from the bore in the tubular enclosure.

To open the enclosure, firstly the spacer 12 is displaced rightwards by pulling on the rod 13, until the spacer abuts against face 25 of the drawer 14. This position is shown in FIG. 4. By continuing to pull rightwards on the rod 13, the drawer 14 is then displaced, and this, by means of the ramps and grooves 20, 21, causes the plug 11 to descend axially. Once the plug 11 has come into abutment against the plugging body 15, it has become axially disengaged from the bore 18 in the enclosure 1, and the drawer abuts rightwards against the left face 26 of the T-shaped section member 28 of the plugging body 15. This position is shown in FIG. 5. The holes 30 and 31 in the drawer 14, and in the plugging body 15 then coincide. By continuing the movement, the plugging body is then driven rightwards until it abuts against the yoke 9 via its left abutment 10. This position is shown in FIG. 6, in which the tubular enclosure 1 is open, with the plug 11 being offset transversely, and the respective holes 30 and 31 in the yoke and in the plugging body coincide with the bore 18 in the enclosure, thereby providing an unobstructed passage through which to feed in the substances to be treated that are packaged in flexible packets 5, or enabling them to be unloaded, depending on whether the plugging device 2 is on the left or on the right of the installation as shown in FIG. 1.

In this way, the enclosure is opened by applying a single traction movement to the rod 13. However, for closure, it is necessary to act in the opposite direction successively firstly on the plugging body 15, then on the drawer 14, and finally on the fork-shaped spacer 12.

In its plugging body 15, the top plugging device 2 (situated on the right of the installation as shown in FIG. 1) is provided with an orifice 32 for feeding in water. This orifice is shown in FIG. 6. Once it has been closed at both of its ends, the enclosure is pressurized via a pipe 33 opening into a channel 34 in the plug 11. This pressurization facility may be installed either on the top plugging device, or on the bottom plugging device.

Figure 8:
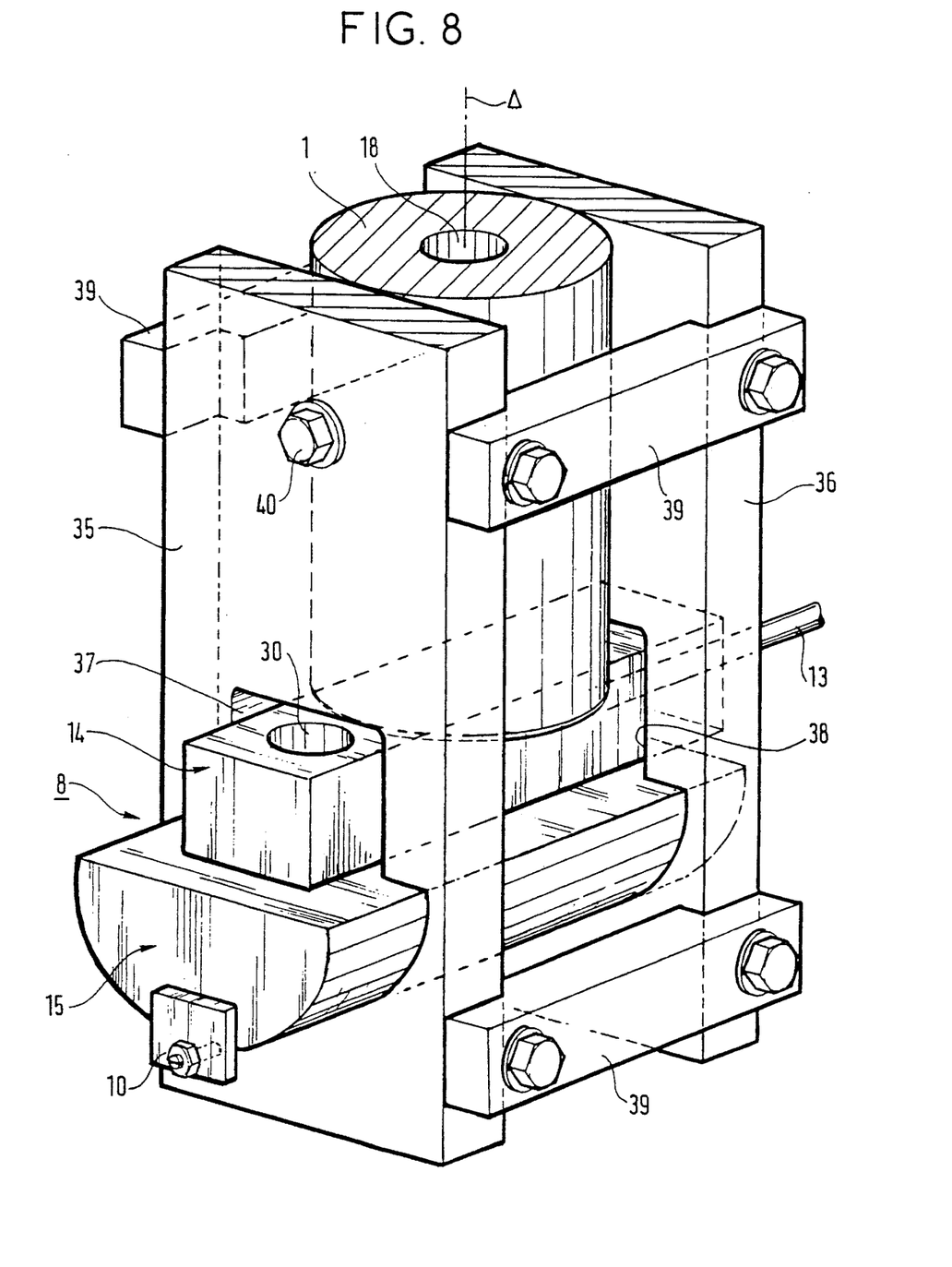
FIG. 8 is a perspective view showing a variant of the force take-up member that supports a plugging device in an installation of the invention.

FIG. 8 shows a variant embodiment in which the force take-up member for the moving assembly 8 of the plugging device is not constituted by a yoke screwed onto the enclosure, but rather by a frame which surrounds the assembly formed by the enclosure and by both of the plugging devices. It essentially comprises two thick sheet metal strips 35 and 36 situated on either side of the enclosure 1, and provided with openings 37, 38 through which the moving assemblies 8 can pass, the strips being interconnected by bars 39. Screws such as 40 are used to support the enclosure 1.

The entire installation may be either sloping, as shown in FIG. 1, or else vertical.

We claim:

1. An installation for subjecting substances packaged in flexible packets to high pressure treatment, the installation comprising a tubular enclosure and means for introducing a fluid under pressure into said enclosure, said enclosure having an axis Δ that is provided with a plugging device at each of its ends, wherein each of said plugging devices includes a moving assembly that can be displaced in a transverse direction γ that is perpendicular to axis Δ, said moving assembly being supported by a force take-up member in which it can slide between two abutment end positions, said moving assembly including a plug including a male portion which is provided with a seal, and which penetrates into a bore in the tubular enclosure, the plug being axially displaced by co-operating with a drawer via a set of ramps and sloping grooves, said drawer being mounted to slide in said transverse direction γ between two stop positions on a plugging body which is itself slidably mounted in said force take-up member, the end position in one direction of said drawer and of said plugging body constituting an open position and guaranteeing that the enclosure is fully open with the plug being both axially and transversely disengaged from the bore in the tubular enclosure, an association of orifices in said plugging body and drawer further guaranteeing, in that end position, an unobstructed axial passage to the bore in the tubular enclosure.

2. An installation according to claim 1, wherein said plug is provided with a stem which penetrates into an orifice in said plugging body.

3. An installation according to claim 1, wherein the end position in a second direction of said drawer and of said plugging body constitutes a closed position wherein a spacer is disposed between said plug and said plugging body.

4. An installation according to claim 3, wherein said spacer is provided with a pull rod via which to apply traction in said transverse direction γ, such traction being applied to said rod causing the spacer to be disengaged by being displaced until it comes into abutment against one end of said drawer, whereupon, with the movement being continued, it drives the drawer with it until the drawer comes into abutment against a stop on the plugging body, whereupon the plugging body is displaced to the final open position in which it abuts against the force take-up member.

5. An installation according to claim 1, wherein said force take-up member is a yoke screwed onto one of said ends of said tubular enclosure.

6. An assembly according to claim 1, wherein said force take-up member is constituted by a frame surrounding the tubular enclosure over its entire length, and over its plugging devices.

* * * * *